United States Patent [19]

Bucolo et al.

[11] 4,087,331
[45] May 2, 1978

[54] COLORIMETRIC METHOD FOR DETERMINING GAMMA-GLUTAMYL TRANSPEPTIDASE AND COMPOSITIONS USEFUL THEREIN

[75] Inventors: Giovanni Bucolo, Hialeah; Mathew M. Madappally, Cooper City; Gerald E. Jaffe, Miami, all of Fla.

[73] Assignee: Coulter Electronics, Inc., Hialeah, Fla.

[21] Appl. No.: 758,800

[22] Filed: Jan. 12, 1977

[51] Int. Cl.$^2$ ...................... G01N 33/00; G01N 31/14
[52] U.S. Cl. ............................... 195/99; 195/103.5 R
[58] Field of Search ........................... 195/99, 103.5 R

[56] References Cited
U.S. PATENT DOCUMENTS

| 3,892,631 | 7/1975 | Carroll | 195/103.5 R |
| 3,986,931 | 10/1976 | Bernt et al. | 195/103.5 R |

OTHER PUBLICATIONS

Goldbarg et al. Arch. Biochem. and Biophys., 91, (1960) pp. 61–70.

Primary Examiner—Alvin E. Tanenholtz
Assistant Examiner—C. A. Fan
Attorney, Agent, or Firm—Silverman, Cass & Singer, Ltd.

[57] ABSTRACT

A colorimetric method for the determination of gamma-glutamyl transpeptidase enzyme activity in a biological fluid comprises catalytically reacting the enzyme in the fluid with a substrate of a water-soluble salt of a compound selected from the group consisting of L-gamma-glutamyl-3-sulfoanilide and L-gamma-glutamyl-4-sulfoanilide in aqueous solution to produce the corresponding aniline sulfonic acid salt as a cleavage product, diazotizing the cleavage product, and coupling the diazotized product with a coupling compound to produce a dye having a color intensity proportional to the enzyme activity.

9 Claims, No Drawings

COLORIMETRIC METHOD FOR DETERMINING GAMMA-GLUTAMYL TRANSPEPTIDASE AND COMPOSITIONS USEFUL THEREIN

BACKGROUND OF THE INVENTION

This invention relates to a colorimetric method for the quantitative determination of gamma-glutamyl transpeptidase enzyme activity in a biological fluid, especially in human blood serum, and to compositions useful in the method.

Gamma-glutamyl transpeptidase is an enzyme which cleaves the C-terminal amino acid, glutamic acid of proteins and peptides. Serum gamma-glutamyl transpeptidase activity is elevated in patients with hepatobiliary tract disease. Extremely high values are usually associated with metastatic cancer of the liver and common bile duct obstruction due to neoplasms. High gamma-glutamyl transpeptidase values also have been reported in patients with various other liver diseases, neurologic disease and post-myocardial infarction. In hepatobiliary disease, the change in gamma-glutamyl transpeptidase activity is a more sensitive indicator than alkaline phosphatase and leucine aminopeptidase. The determination of gamma-glutamyl transpeptidase activity in serum has been shown to be a valuable aid in clinical diagnosis.

Gamma-glutamyl transpeptidase in biological materials is assayed by a transferase reaction, in which the enzyme acts catlytically upon a substrate of a synthetic peptide of L-glutamic acid, having a C-terminal glutamyl radical and a free carboxyl group, to transfer the glutamyl radical to a receptor having an L-amino acid moiety, including amino acids and peptides. The quantity of the cleavage product resulting from the transfer of the glutamyl radical from the synthetic peptide is determined as a measure of the activity of the enzyme.

The most commonly employed substrate for the assay of gamma-glutamyl transpeptidase is L-glutamyl-p-nitroanilide (J. Biol. Chem., 240, 338 (1965); Clin. Chem., 15, 124 (1969)). The cleavage product of the enzyme reaction, p-nitroaniline, produces a strongly yellow-colored solution. The coloration can be followed kinetically by the increase in light absorption at 405 nanometers (nm). The same substrate has been employed in an assay method in which the cleavage product is diazotized by nitrous acid and then coupled with 8-hydroxyquinoline sulfate (U.S. Pat. No. 3,878,048). The substrate has the disadvantage that it is very poorly soluble in the aqueous media employed for assay, and therefore an elevated temperature (60° C) and/or a surfactant must be used to solubilize the substrate. Owing to the low solubility, the assay is performed in the presence of limiting quantities of the substrate.

The solubility of the substrate was increased by the introduction of a sulfonic group in the 3-position of the p-nitroaniline, to provide gamma-glutamyl-3-sulfonic acid-4-nitroanilide (German published application No. 23 33 798), and by the introduction of a carboxyl group in the 3-position, to provide gamma-glutamyl-3-carboxy-4-nitroanilide (German published application No. 22 59 512; see also J. Clin. Chem. Clin. Biochem. 14, 421 (1976). When the assay is followed kinetically, the products released have an absorbance in the range of 350–450nm. In this range the absorbance of hemolyzed, icteric or turbid samples represent a strong interference. This is a definite disadvantage. Furthermore, stability of reagents in solution is limited, as reported in the latter paper.

The solubilities of the several compounds as based upon the literature are as follows:

| Substrate | Solubility, g./liter |
|---|---|
| gamma-glutamyl-p-nitroanilide | 1–1.25 |
| gamma-glutamyl-3-sulfonic-4-nitroanilide, as NH$_4$ salt | 100–125 |
| gamma-glutamyl-3-carboxylic-4-nitroanilide, as di-NH$_4$ salt | 20–25 |

A similar assay method employed gamma-glutamyl aniline as the substrate (Arch. Biochem. and Biophys., 91, 61 (1960)). The aniline cleavage product was diazotized and coupled with N-(1-naphthyl)ethylenediamine in the form of its dihydrochloride addition salt, by a modified Bratton-Marshall procedure (J. Biol. Chem., 128, 537 (1939)). This substrate, however, exhibits poor stability in solution. It also requires heat and/or a surfactant to solubilize the substrate. Owing to the low solubility, the assay is performed in the presence of limiting quantities of the substrate. The upper limit of linearity is low (up to 130 milliunits of enzyme activity per milliliter) and, therefore, frequent dilution of samples with high activity is required.

Another synthetic peptide substrate which has been employed is gamma-glutamyl-alpha-naphthylamide (Clin. Chim. Acta, 14, 619 (1966)). The cleavage product of enzyme reaction is alpha-naphthylamine, which is coupled to the diazonium compound, Fast Blue B salt, to form a strongly colored dye. The development of the color is a relatively slow process, and alpha-naphthylamine has been found to be carcinogenic.

SUMMARY OF THE INVENTION

This invention relates to an improved colorimetric method for the determination of gamma-glutamyl transpeptidase enzyme activity in a biological fluid, wherein a water-soluble salt of a compound selected from the group consisting of L-gamma-glutamyl-3-sulfoanilide and L-gamma-glutamyl-4-sulfoanilide is employed as a substrate in aqueous medium, the substrate is acted upon catalytically by the enzyme in the fluid to yield a diazotizable cleavage product, the cleavage product is diazotized, and the diazotized product is reacted with a coupling compound to produce a dye having a color intensity proportional to the enzyme activity. The preferred coupling compound is N-(1-naphthyl)ethylenediamine, employed in water-soluble salt form.

The invention provides new compounds useful in the assay method, which are the gamma-glutamylsulfoanilides having the following structural formulae:

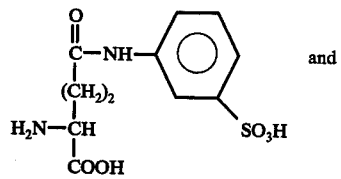

L-√-glutamyl-3-sulfoanilide

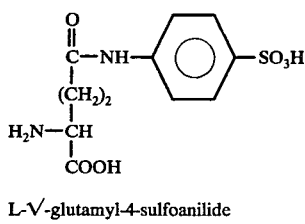

L-γ-glutamyl-4-sulfoanilide and their water-soluble salts. The invention also provides a new substrate solution for use in assaying the enzyme, as set forth hereinafter.

The invention provides numerous advantages, including ready solubility of the new substrate in water, at least 300 grams per liter; ability to use an excess amount of substrate, for greater accuracy and measurement of very high enzyme activity; stability of the subtrate; a substrate solution pH of 7.2, which is very close to the pH of serum; rapid reaction of the enzyme with the substrate; an enzyme reaction with the substrate which is linear with time; rapid diazotization of the cleavage product; instantaneous coupling of the diazotized product with a coupling compound; an intense color reaction, providing an accurate measurement of the activity in the normal range; and color stability greater than one hour, permitting many assays to be performed at the same time.

DESCRIPTION OF THE PREFERRED EMBODIMENTS

In accordance with a preferred embodiment of the invention, gamma-glutamyl transpeptidase enzyme activity is determined in human blood serum, including plasma. The serum is incubated with an aqueous solution containing a compound selected from the group consisting of L-gamma-glutamyl-3-sulfoanilide and L-gamma-glutamyl-4-sulfoanilide in water-soluble salt form, preferably employed in an excess amount with respect to the ability of the enzyme to react with the substrate in the time allotted for assay. The 3-isomer appears to be a better substrate for the enzyme; thus gamma-glutamyl transferase is more active (3 times) with this substrate than with the 3-isomer. This product is however more expensive to synthesize and the increased cost would offset the advantage offered by the greater sensitivity. The molar extinction coefficient of the two reaction products is the same.

The water-soluble salt of the L-gamma-glutamyl-sulfoanilide preferably is an alkali metal or ammonium sulfonate salt, i.e., a monosubstituted salt in which the sulfonic acid radical is reacted. Other soluble salts which might be employed include the monosubstituted magnesium salt and the salts formed with tris(hydroxymethylamino) methane, 2-amino-2-methyl-1, 3-propanediol, 2-amino-2-methyl-1-propanol, and aliphatic amines, such as ethylamine, triethylenetetramine, 2-ethylhexylamine, diethylamine, trimethylamine, and tributylamine.

The reaction takes place in the presence of a receptor of the glutamyl radical, which is provided in the substrate solution. The preferred receptor is glycyl glycine. Other receptors for the glutamyl radical may be employed, such as asparagine, methionine, L-phenylalanine, and hydroxylamine.

The substrate solution preferably is buffered to a pH of about 7.2. The preferred buffer is tris(hydroxymethyl)aminomethane hydrochloride ("Tris HCl"). Other buffers may be employed, such as Ammediol hydrochloride (2-amino-2-methylpropane-1,3-diol hydrochloride).

Sodium nitrite is included in the substrate solution, for diazotization of the cleavage product. It does not affect the enzyme activity.

Sodium chloride preferably is included in the substrate solution. It assists in clearing the solution, and it has a beneficial effect in increasing the sensitivity.

A surfactant preferably is included in the substrate solution, to maintain the cleavage product is solution and to stabilize the color. A non-ionic surfactant is preferred, particularly, an alkylene oxide ether of a long chain fatty alcohol, such as a polyoxyethylene ether of such an alcohol. A preferred surfactant is the 23-mole ethylene oxide ether of lauryl alcohol, having a molecular weight of 1199.57 (Brij 35).

A preferred substrate solution is an aqueous solution having a pH of about 7.2 and containing the following materials in the proportions indicated:

| Material | Amount Per Liter |
| --- | --- |
| Sodium sulfonate salt of L-gamma-glutamyl-3-sulfoanilide or L-gamma-glutamyl-4-sulfoanilide | 2.5–5 millimoles |
| Glycyl glycine | 130–210 millimoles |
| Sodium nitrite | 0.5–2 millimoles |
| Tris(hydroxymethyl)aminomethane hydrochloride | 10–100 millimoles |
| Sodium chloride | 3–5 millimoles |
| Polyoxyethylene (23) lauryl ether | 1–2 grams |

Where the materials as employed provide a different pH in solution, the pH may be adjusted to the preferred value by the addition of sodium hydroxide or hydrochloric acid, as required. The rate of decay of the substrate in the solution is slow, permitting use of the solution after storage for two days at ambient temperature and after storage for fifteen days in the refrigerator.

It is preferred to mix the foregoing substrate solution with a blood serum sample to be assayed in a volume ratio of about 6–10 parts of solution to one part of sample. The mixture is incubated for a predetermined time at a specified temperature. A temperature of about 37° C. is preferred. The reaction of the enzyme on the substrate is linear with time for at least 18 minutes at this temperature. Incubation of serum with very low enzyme activity releases as appreciable amount of the cleavage product, anilinesulfonic acid, in the form of the sodium sulfonate, during the first 10 minutes of incubation. Therefore, a 10-minute incubation period is sufficient and preferred.

The enzyme-catalyzed transferase reaction which takes place during incubation may be represented as follows:

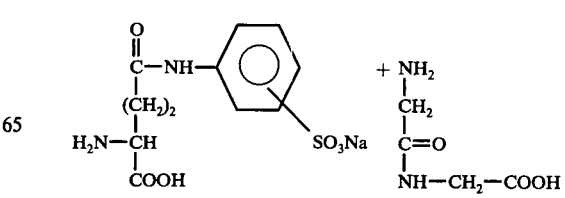

-continued

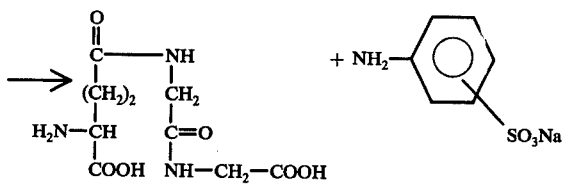

The enzyme is inactivated at the end of the incubation period, and the anilinesulfonic acid cleavage product is diazotized. Acidification of the reaction medium serves both purposes. For rapid diazotization and coupling, the pH of the solution preferably is lowered to a maximum of about 1.6. A preferred reagent for this purpose is 0.5M hydrochloric acid. Alternatively, a dry solid acid may be employed, for convenience in distribution, storage and handling, such as oxalic acid. The acid is mixed with the reaction solution and allowed to react for a minimum time of about 1 minute, which is sufficient for diazotization.

The diazonium salt in the reaction medium is reacted with a coupling compound or coupler to produce a dye having a color intensity proportional to the enzyme activity. Various coupling compounds may be employed, of which N-(1-naphthyl)ethylenediamine is preferred. Other useful coupling compounds include N,N-dimethyl-1-naphthylamine, N-(1-naphthyl)glucamine, N,N-di-(hydroxyethyl)-1-naphthylamine, sulfonated N-ethyl-1-naphthylamine, 1-napthol-4-sulfonic acid, 2-naphthol-3,6-disulfonic acid, p-phenolsulfonic acid, 2-naphthol-6,8-disulfonic acid, 1-naphthol-3,8-disulfonic acid, resorcinol, 8-amino-1-naphthol-3,6-disulfonic acid, N-sulphatoethyl-m-toluidine, 3-hydroxy-2-naphthoic acid, and N'-diethyl-N-1-naphthylpropylene diamine. The coupling compounds are employed in water-soluble salt form as may be appropriate, e.g., in the form of their acid addition salts, such as their hydrochlorides, or as their alkali metal salts, such as their sodium salts, as the case may be.

N-(1-naphthyl)ethylenediamine is preferred because it is readily available in a high degree of purity, and long has been employed in the clinical laboratory. it is employed in water-soluble salt form, preferably, as an acid addition salt, such as the dihydrochloride. The dihydrochloride salt is employed in aqueous solution at a preferred concentration of about 10 gm./liter. At this concentration, about five volumes of the coupler solution are employed per volume of the blood serum sample.

Coupling takes place instantaneously, to form a pink azo dye having a very intense color which is stable for more than one hour. The color formed has an absorption maximum at 535 nm, and its intensity is proportional to the enzymatic activity. The intensity of light absorption by the resulting solution is measured at 535 nm, and it may be read immediately following addition of the coupler.

The assay solution is run against a solution made up of the substrate solution, the acid, and the coupler solution, and the sample is omitted, substituting an equal volume of water therefor. The preferred method of determining the enzyme activity embodies the use of a calibrator of known gamma-glutamyl transpeptidase activity. The calibrator is treated in the same manner as the sample, and the absorbances of the two final products compared. The activity in the sample can be calculated from the absorbances and the known activity of the calibrator. Alternatively, the results obtained with the sample may be compared with the results obtained when an anilinesulfonic acid standard is treated in the same manner as the sample. The enzyme activity may be calculated from the amount of aniliesulfonic acid cleavage product formed, as thus determined.

Employing the foregoing method, samples having activities up to 600 milliunits per milliliter, or 600 international units per liter of gamma-glutamyl transpeptidase activity, which is 15 times the upper limit of normal, may be assayed without dilution. The entire assay procedure can be completed within fifteen minutes.

The gamma-glutamylsulfoanilides employed in the new method are produced from the known compound, phthaloyl-DL-glutamic anhydride (J. Am. Chem. Soc., 72, 2469 (1950); J. Chem. Soc., 3 315 (1949) by the method of German published patent application No. 23 33 798 for the preparation of gamma-glutamyl-3-sulfonic acid-4-nitroanilide. The reaction sequence may be represented as follows:

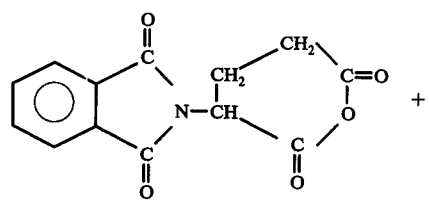

Phthaloyl-DL-Glutamic Anhydride

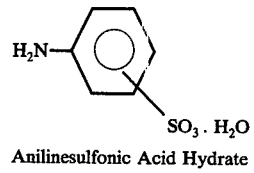

Anilinesulfonic Acid Hydrate

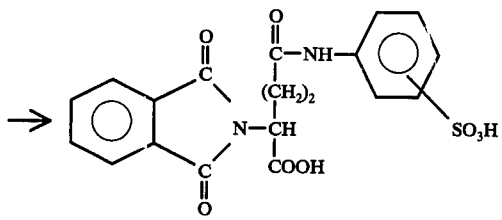

Phthaloyl-DL-Gamma-Glutamylsulfoanilide

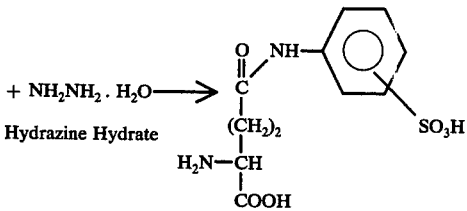

DL-Gamma-Glutamylsulfoanilide

Use of aniline-3-sulfonic acid and aniline-4-sulfonic acid as the starting material yields as the final product gamma-glutamyl-3-sulfoanilide and gamma-glutamyl-4-sulfoanilide, respectively. The product in each case is the racemic (DL) mixture. The L-isomer is the substrate for the enzyme gamma-glutamyl transpeptidase. Since the D-isomer is not an inhibitor, the racemic mixture can be used for the assay. The preferred alkali metal and ammonium sulfonate salts of the gamma-glutamylsulfoanilides are prepared by neutralization of the latter compounds with alkali metal hydroxide or ammonium hydroxide, corresponding to the desired salt, and other salts are prepared by appropriate methods.

The following examples are furnished to illustrate the preferred practice of the invention. It will be understood that the invention is not limited to the materials, proportions, conditions and procedures set forth therein, which are merely illustrative.

EXAMPLE 1

Compounds for use as substrates in the assay method were produced by the following procedure: A 13.2 gm. quantity of phthaloyl-DL-glutamic anhydride was dissolved in 65 ml. of dimethyl formamide, and a 9.55 gm. quantity of aniline-3-sulfonic acid or aniline-4-sulfonic acid was added. The mixture was refluxed for several hours and then concentrated under reduced pressure (20-30 mm. Hg). affording a viscous orange-brown colored oil of phthaloyl-DL-gamma-glutamyl-3 or 4-sulfoanilide.

The oily product was dissolved in 500 ml. of methanol, and a 10 gm. quantity of hydrazine hydrate was added. After filtering to remove a small amount of an insoluble material, the filtrate was stirred at room temperature for 48 hours. The resulting colorless solid was separated by filtration and suspended in 300 ml. of water. The mixture was stirred for 30 minutes and then filtered. The filtrate was freeze-dried, to yield a solid product of DL-gamma-glutamyl-3 or 4-sulfoanilide.

The product was suspended in 3 parts by volume of water and adjusted to pH 7 by the addition of concentrated aqueous sodium hydroxide solution. The resulting solution was added to 20 parts by volume of acetone, with vigorous stirring. A precipitate formed and was washed with hot methanol. The resulting product was the sodium sulfonate salt of DL-gamma-glutamyl-3 or 4-sulfoanilide, in which the position of the sulfonate radical corresponded to the aniliesulfonic acid starting material.

EXAMPLE 2

Gamma-glutamyl transpeptidase activity in human blood serum is determined in a preferred manner employing three reagent solutions, i.e., a substrate solution, an acid solution for enzyme inactivation and diazotization, and a coupler solution for color development.

The substrate solution has a pH of about 7.15 to 7.2 and contains the following materials dissolved in deionized water in the proportions indicated:

| Material | Amount Per Liter |
| --- | --- |
| Sodium salt of DL-gamma-glutamyl-3 or 4-sulfoanilide | 8 millimoles |
| Glycyl glycine | 167 millimoles |
| Sodium nitrite | 1.39 millimoles |
| Tris(hydroxymethyl)aminomethane hydrochloride | 84 millimoles |
| Sodium chloride | 4.2 millimoles |
| Polyoxyethylene(23) lauryl ether (Brij 35) | 1.7 grams |

The acid solution is 0.5M hydrochloric acid or 0.5M oxalic acid. The coupler solution contains 10 gms./liter of N-(1-naphthyl)ethylenediamine dihydrochloride in deionized water.

A 1.6 ml. quantity of the substrate solution is pipetted into a test tube, and 0.2 ml. of a sample of human blood serum is added to the test tube and mixed with the substrate solution. The mixture is incubated at 37° C for 10 minutes. A 0.9 ml. quantity of the acid solution is added to the test tube, mixed with the contents, and allowed to stand at least one minute. A 1 ml. quantity of the coupler solution is added to the test tube and mixed with the contents.

The light absorbance of the pink-colored solution is read at 535 nm against a solution prepared in the same manner but substituting 0.2 ml. of deionized water for the sample. The absorbance of a gamma-glutamyl transpeptidase enzyme control serum of known activity is determined in the same manner. The gamma-glutamyl transpeptidase enzyme activity of the test sample is calculated employing the following equation:

$$\text{Sample activity} = \frac{\text{Absorbance of sample} \times \text{Control activity}}{\text{Absorbance of control}}$$

We claim:

1. In a colorimetric method for the determination of gamma-glutamyl transpeptidase enzyme activity in a biological fluid, wherein said enzyme in said fluid is reacted catalytically with a substrate of a synthetic peptide of L-glutamic acid in aqueous medium to yield a diazotizable cleavage product of the peptide and the cleavage product is diazotized and reacted with a coupling compound to produce a dye having a color intensity proportional to the enzyme activity, the improvement which comprises employing as said substrate a water-soluble salt of a compound selected from the group consisting of L-gamma-glutamyl-3-sulfoanilide and L-gamma-glutamyl-4-sulfoanilide.

2. The method defined in claim 1 wherein said substrate is a water-soluble salt of L-gamma-glutamyl-3-sulfoanilide.

3. The method defined in claim 1 wherein said substrate is a water-soluble salt of L-gamma-glutamyl-4-sulfoanilide.

4. The method defined in claim 1 wherein said coupling compound is N-(1-naphthyl)ethylenediamine.

5. A colorimetric method for the determination of gamma-glutamyl transpeptidase enzyme activity in a biological fluid which comprises catalytically reacting said enzyme in said fluid with a substrate of a water-soluble salt of a compound selected from the group consisting of L-gamma-glutamyl-3-sulfoanilide and L-gamma-glutamyl-4-sulfoanilide in aqueous solution to produce the corresponding aniline sulfonic acid salt as a cleavage product, diazotizing said cleavage product, and coupling the diazotized product with N-(1-naphthyl)ethylenediamine in water-soluble salt form.

6. The method defined in claim 5 wherein said fluid comprises human blood serum.

7. A colorimetric method for the determination of gamma-glutamyl transpeptidase enzyme activity in human blood serum which comprises incubating the serum with an aqueous substrate solution having a pH of about 7.2, containing an excess amount of the sodium sulfonate salt of a compound selected from the group consisting of L-gamma-glutamyl-3-sulfoanilide and L-gamma-glutamyl-4-sulfoanilide, and containing glycyl glycine as a receptor of the glutamyl radical at about 37° C and for a period of time of about 10 minutes to produce the corresponding aniline sodium sulfonate as a cleavage product, inactivating said enzyme, diazotizing said cleavage product in the resulting solution with nitrous acid, adding to the resulting solution N-(1-naphthyl)ethylenediamine in water-soluble salt form for coupling with the diazotized product to form a dye, and measuring the intensity of light absorption by the resulting solution at 535 nanometers.

8. The method defined in claim 7 wherein said enzyme inactivation and diazotization are accomplished by lowering the solution pH to a maximum of about 1.6.

9. A substrate solution for reaction with gamma-glutamyl transpeptidase enzyme in a colorimetric method for the determination of the activity of the enzyme in a biological fluid, which comprises an aqueous solution having a pH of about 7.2 and containing the following materials in the proportions indicated:

| Material | Amount Per Liter |
| --- | --- |
| Sodium sulfonate salt of L-gamma-glutamyl-3-sulfoanilide or L-gamma-glutamyl-4-sulfoanilide | 2.5–5 millimoles |
| Glycyl glycine | 130–210 millimoles |
| Sodium nitrite | 0.5–2 millimoles |
| Tris(hydroxymethyl)aminomethane hydrochloride | 10–100 millimoles |
| Sodium chloride | 3–5 millimoles |
| Polyoxyethylene(23) lauryl ether | 1–2 grams. |

* * * * *